(12) United States Patent
Pollonini et al.

(10) Patent No.: US 11,172,852 B2
(45) Date of Patent: Nov. 16, 2021

(54) METHOD FOR MEASURING PHYSIOLOGICAL PARAMETERS OF PHYSICAL ACTIVITY

(71) Applicant: UNIVERSITY OF HOUSTON SYSTEM, Houston, TX (US)

(72) Inventors: Luca Pollonini, Manvel, TX (US); Clifford C. Dacso, Bellaire, TX (US)

(73) Assignee: University of Houston System, Houston, TX (US)

(*) Notice: Subject to any disclaimer, the term of this patent is extended or adjusted under 35 U.S.C. 154(b) by 285 days.

(21) Appl. No.: 16/381,873

(22) Filed: Apr. 11, 2019

(65) Prior Publication Data

US 2019/0239785 A1 Aug. 8, 2019

Related U.S. Application Data

(62) Division of application No. 14/662,801, filed on Mar. 19, 2015, now Pat. No. 10,292,629.

(60) Provisional application No. 61/955,442, filed on Mar. 19, 2014.

(51) Int. Cl.
*A61B 5/1455* (2006.01)
*A61B 5/11* (2006.01)
*A61B 5/145* (2006.01)
*A61B 5/024* (2006.01)
*A61B 5/00* (2006.01)

(52) U.S. Cl.
CPC ........ *A61B 5/14551* (2013.01); *A61B 5/1107* (2013.01); *A61B 5/1118* (2013.01); *A61B 5/14546* (2013.01); *A61B 5/024* (2013.01); *A61B 5/1112* (2013.01); *A61B 5/1123* (2013.01); *A61B 5/6831* (2013.01); *A61B 5/6898* (2013.01); *A61B 5/7225* (2013.01)

(58) Field of Classification Search
CPC .............. A61B 5/14551; A61B 5/1107; A61B 5/14546; A61B 5/1118; A61B 5/7225; A61B 5/6831; A61B 5/6898; A61B 5/024; A61B 5/1123; A61B 5/1112
See application file for complete search history.

(56) References Cited

U.S. PATENT DOCUMENTS

| | | |
|---|---|---|
| 2003/0120485 A1 | 6/2003 | Murase et al. |
| 2005/0253047 A1 | 11/2005 | Maegawa et al. |
| 2006/0063995 A1 | 3/2006 | Yodh et al. |
| 2006/0079794 A1 | 4/2006 | Liu et al. |
| 2013/0096403 A1 | 4/2013 | Dacso et al. |
| 2013/0144140 A1 | 6/2013 | Frederick et al. |
| 2013/0274573 A1 | 10/2013 | McCully et al. |
| 2013/0332286 A1 | 12/2013 | Medellus et al. |

OTHER PUBLICATIONS

International Search Report and Written Opinion issued in PCT Application No. PCT/US2015/021546 dated Jun. 29, 2015.
Non-Final Office Action issued in U.S. Appl. No. 14/662,801.

*Primary Examiner* — Mark W. Bockelman
(74) *Attorney, Agent, or Firm* — Parker Highlander PLLC

(57) ABSTRACT

The present disclosure generally relates to methods of using near infra-red radiation, such as from a near infra-red spectroscopy device, to monitor physical activity in a person. In one aspect, a method of measuring physiological parameters is provided. The method further includes determining a NIRS-derived measure of a tissue of a person using near infra-red spectroscopy over a time period, associating the NIRS-derived measure to the time period to determine a function-related change, and associating the function-related change to a biomechanical function.

4 Claims, 9 Drawing Sheets

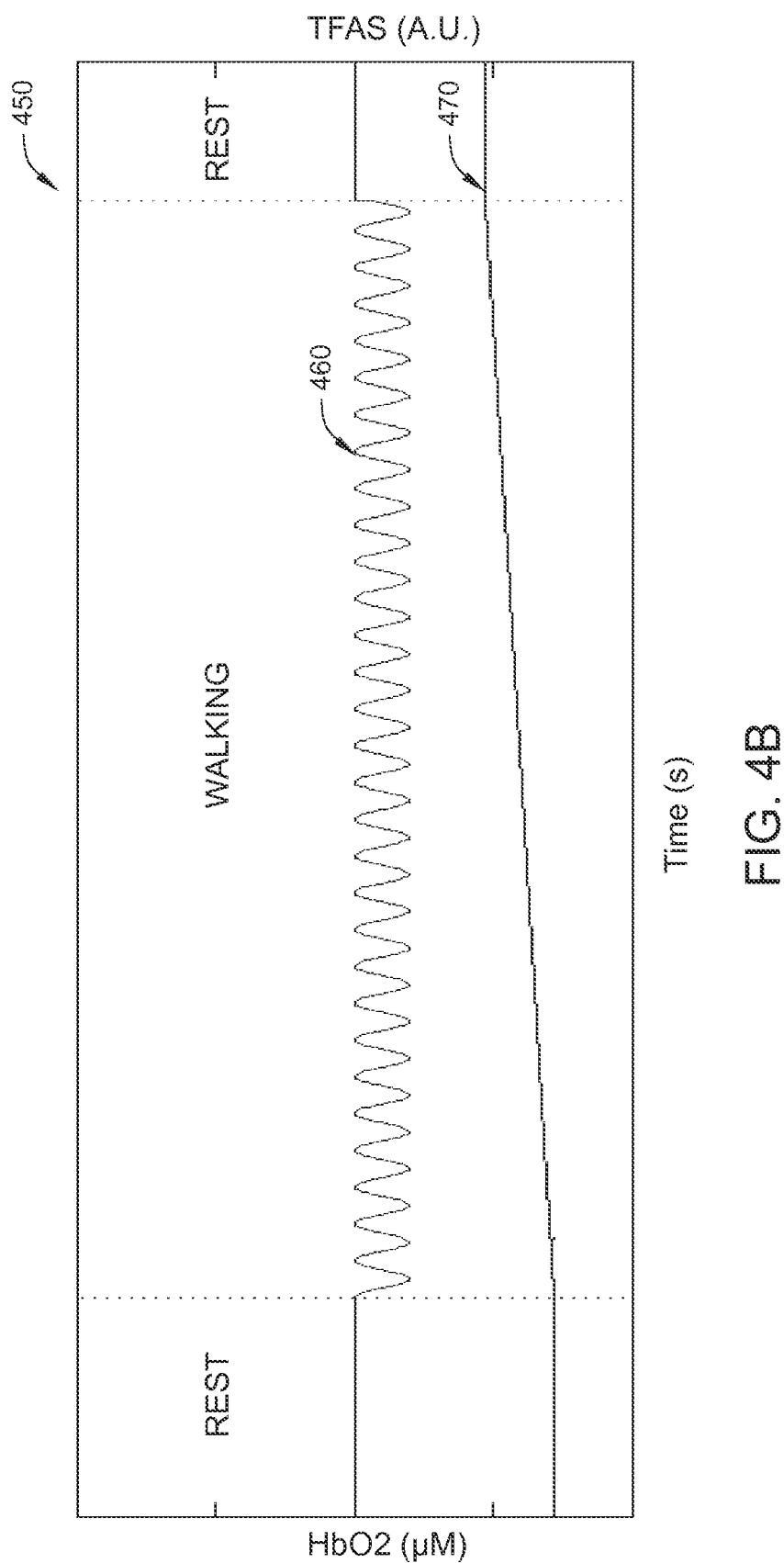

METHOD FOR MEASURING PHYSIOLOGICAL PARAMETERS OF PHYSICAL ACTIVITY

CROSS-REFERENCE TO RELATED APPLICATIONS

This application is a divisional application of U.S. patent application Ser. No. 14/662,801 filed on Mar. 19, 2015, and claims priority to U.S. Provisional Patent Application Ser. No. 61/955,442, filed on Mar. 19, 2014, the entirety of each is incorporated by reference herein.

BACKGROUND

Field

Embodiments of the present invention generally relate to methods of monitoring physical activity. More particularly, the embodiments generally relate to methods for real-time assessment of physical activity over a period of time using near infra-red spectroscopy.

Description of the Related Art

Parameters of physical activity, such as oxygen use, heart rate and stride length, provide helpful indicators for performance of both athletes and the casual exerciser alike. Current methodologies used for measurement of parameters of physical activity vary and depend on the physical quantity being measured. For instance, running cadence in the field is currently measured with wearable accelerometers. Similar technologies are also used as step counters, i.e. in pedometers. Pedaling cadence is also measurable with accelerometers or with sensing equipment mounted on the bike, e.g. proximity sensors. Energy expenditure is currently measured with indirect and direct calorimetric and noncalorimetric methods. However, though cheap and easy to employ, the precision of these measurements are inherently limited.

Where high accuracy is required and sufficient resources are available, an open-circuit indirect calorimeter has previously been used. Open-circuit indirect calorimeters employ a mask, hood, canopy or room/chamber for collection of expired air. For short-term measurements, mask, hood or canopy systems suffice. Chamber-based systems are more accurate for the long-term measurement of specified activity patterns but behavior constraints mean they do not reflect real life. Overall, open-circuit indirect calorimeters and related methods are inherently invasive, time consuming, costly and cumbersome.

Therefore, there is a need for improved methods of exercise monitoring or monitoring of physical activity.

SUMMARY

Embodiments described herein generally relate to methods of monitoring and analyzing physical activity using near infra-red spectroscopy (NIRS). In one embodiment, a method of measuring physiological parameters can include determining a NIRS-derived measure of a tissue using NIRS over a time period, the time period including a resting period and an active period; associating the NIRS-derived measure as determined during the resting period to the NIRS-derived measure as determined during the active period to determine a function-related change; and associating the function-related change to a biomechanical function.

In another embodiment, a method of measuring physiological parameters can include measuring hemoglobin concentrations in a tissue using NIRS over a first time period, the first time period including a first resting period and a first active period, the hemoglobin concentrations having a first concentration range and a second concentration range; determining the first concentration range using the first resting period and the second concentration range using the first active period; measuring hemoglobin concentrations over a second time period, the second time period having a second resting period and a second active period; and associating the second resting period to the first concentration range and the second active period to the second concentration range.

In another embodiment, a method of measuring physiological parameters can include determining a NIRS-derived measure using NIRS over a time period in each of a plurality of tissues of a person, the time period including a resting period and an active period; associating the NIRS-derived measure as determined during the resting period to the NIRS-derived measure as determined during the active period to determine a function-related change in each of the plurality of tissues; associating the function-related change in each of the plurality of tissues to determine an activity-related change; and associating the activity-related change to a biomechanical activity.

In another embodiment, the method creating a biomechanical profile can include positioning a plurality of NIRS devices at a plurality of sites on an individual, wherein the individual performs a biomechanical function or a biomechanical activity; creating a plurality of NIRS-derived measures over a period of time using the plurality of NIRS devices; analyzing the plurality of NIRS-derived measures to determine one or more measurement features; and associating the one or more measurement features to a portion of the biomechanical function, the biomechanical activity or combinations thereof to create a biomechanical profile.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention, and are therefore not to be considered limiting of its scope, for the invention may admit to other equally effective embodiments.

FIGS. 4A and 4B are graphs of $HbO_2$ as correlated to activity, according to an embodiment described herein;

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The embodiments described herein generally relate to methods for monitoring physical activity using at least one non-invasive biosensor device configured to measure physiological parameters of a subject. The method described uses NIRS at one or more tissue locations on the person to indirectly measure NIRS-derived measures, such as blood flow and oxygenation, which are associated with physical activity remotely from the subject and in a non-invasive fashion. The measured NIRS-derived measures can then be associated with general activity, specific biomechanical movements, or specific biomechanical activities. The near infra-red (NIR) measurement at a tissue can be used alone, in conjunction with another measurement at another tissue, in conjunction with other biosensor devices, such as accelerometers, or combinations thereof to determine a biomechanical function or a biomechanical activity. The embodiments described herein can be more clearly understood with reference to the figures below.

Figure 1:
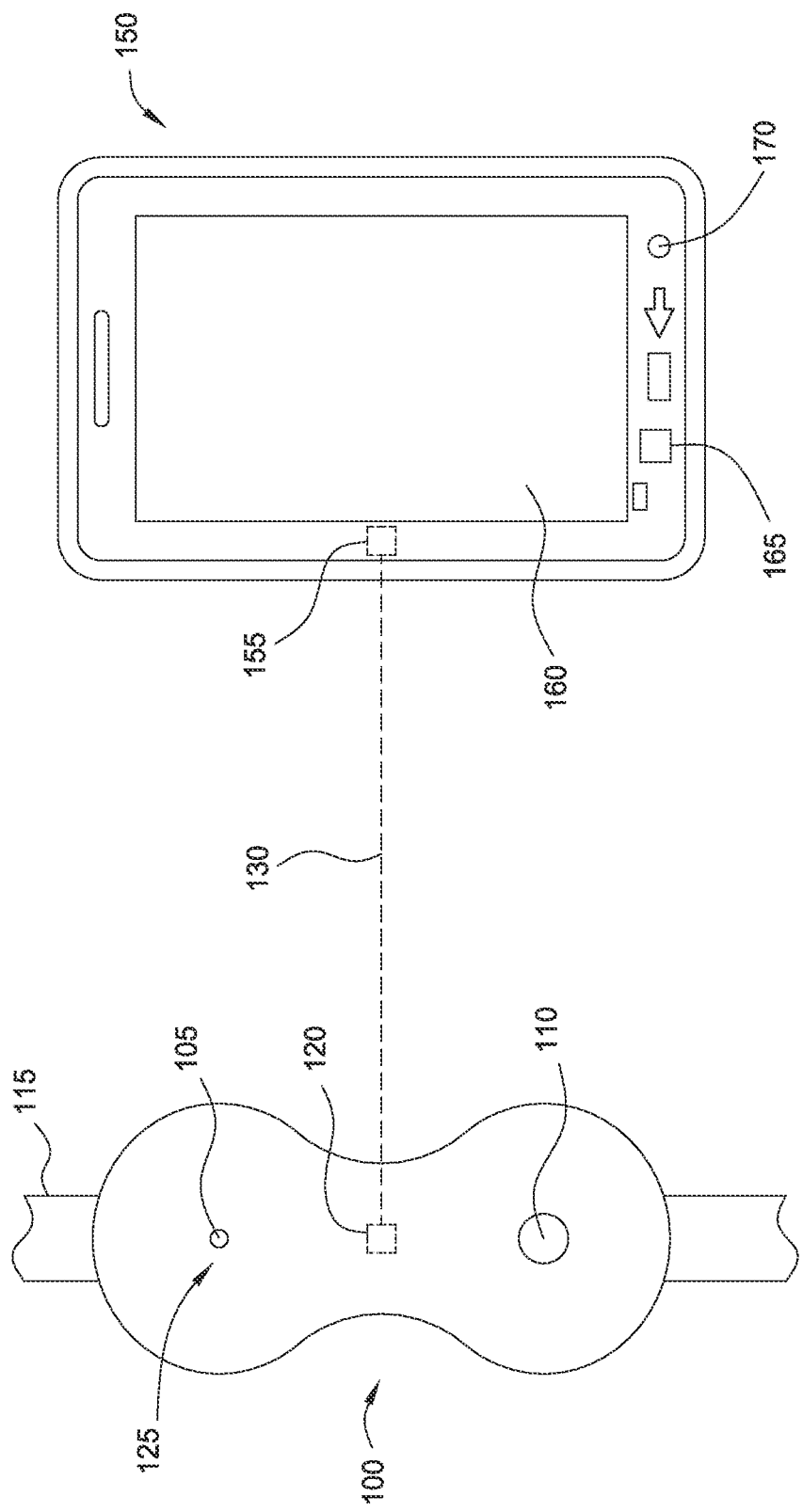
FIG. 1 illustrates a non-invasive biosensor device, according to an embodiment described herein.

FIG. 1 illustrates a non-invasive biosensor device 100. The device 100 may be attached to a subject, such as to a muscle mass via a strap 115. The device 100 will be described herein in relation to lactate threshold or ventilatory threshold. The device 100 may be used with an optional secondary device 150, such as a smartphone (as shown), a watch, computer, mobile phone, tablet, a generic electronic processing and displaying unit, Cloud Storage, or a remote data repository via cellular network, or wireless Internet connection. In one embodiment, the device 100 is NIRS device which is wirelessly connected to a smartphone.

The device 100 includes an optical sensor 125 that uses an optical technique called near infra-red spectroscopy (NIRS). The optical sensor 125 is a unit on the device 100 which both emits and detects radiation to collect raw information regarding the presence of hemoglobin. The optical sensor 125 is configured to measure local NIRS-derived measures, such as oxygenated hemoglobin ($HbO_2$) and deoxygenated hemoglobin (HHb) non-invasively and in real time. The local NIRS-derived measures can then be used to derive secondary parameters such as total hemoglobin present (tHb) and Tissue Oxygenation Index (TOI). The optical sensor 125 includes a radiation source 105 to produce the radiation and a detector 110 to receive the radiation produced by the radiation source 105. In general, the optical sensor 125 uses two or more radiation sources 105, which can include low-power lasers, LED or quasi-monochromatic light sources, and at least one detector 110, such as low-noise photodetecting electronics, to measure the optical absorption of hemoglobin in oxygenated ($HbO_2$) and deoxygenated (HHb) states, water ($HbO_2$), and to calculate the molar concentration of such components in the tissue, such as the skin or a muscle. The molar concentrations of the above described components of the tissue are then calculated using a computer or other processing device adapted for the purpose of processing the data received from the radiation source 105 and the detector 110. In one embodiment, the optical sensor 125 has a skin contact area of 3.5"×2". The device 100 may include a power supply (not shown), such as a battery, to supply power to the optical sensor 125 and other components in the device 100. In another embodiment, the optical sensor 125 can use a broad-spectrum radiation source and a detector sensitive to the spectral components of light, such as a charge coupled device (CCD) spectrometer or other linear photodetector coupled with near infra-red optical filters.

The optical sensor 125 is an optoelectronic instrument, which, in association with hardware and software is able to measure the characteristic optical absorption of a material at certain wavelengths belonging to the near infra-red (NIR) spectrum. From these measurements and elaboration of the data collected, an absolute level of the $HbO_2$ and HHb, can be obtained that enables the oxygenation/saturation of a tissue to be established and displayed in real time. Measurements include data which is directly attributable from the signal, such as concentration of oxygenated hemoglobin. Elaborations are information which is extrapolated from the measurements, such as the TOI. The optical sensor 125 includes the radiation source 105, which is an optical source that generates NIR radiation at a continual intensity. In one embodiment, the optical probe 125 is made up of a preset number of radiation sources 105, such as three or more, whose function is to generate a radiation with wavelength in the NIR spectral range. The optical sensor 125 includes the detector 110, which may be a plurality of detectors that converts the radiation coming from the tissue into an electric signal and amplifies the signal. The optical sensor 125 also includes a control unit that manages the timing of the system, the analog to digital conversion of the measurement signals and that controls the communication with the secondary device 150.

In order for the optical sensor 125 to be able to obtain the [HbO2] and the [HHb], a method is implemented based on the water absorption peak method, using the optical absorption of water at a set wavelength, for example about 980 nm, as a reference to calculate the contribution of the scattering at the same wavelength. Water is the dominant absorbing chromophore at 980 nm. Therefore, assuming that the optical absorption measured at 980 nm is totally due to water implies a reduced or negligible error. Since the concentration of water in muscles is fairly constant at 80% and the extinction coefficient of water at 980 nm is known, it is possible to calculate the scattering coefficient at 980 nm by solving the photon diffusion equation, which is valid for highly scattering media such as human tissues. Given that the scattering coefficient is linearly related with the wavelength of the light, and that the coefficients of this relationship are known for many tissues, once the scattering coefficient at 980 nm has been measured, it can be calculated for the other wavelengths produced by the radiation source 105. The light intensity that exits the tissue at a given geometric distance between the radiation source 105 and the detector 110 is a function of the input optical intensity, the distance between the radiation source 105 and the detector 110, the scattering coefficient and the absorption coefficient. Once the spectrum of the scattering coefficient has been established, and the other variables being known, it is possible to calculate the absorption coefficient at the other wavelengths.

To implement this processing method, it is necessary to illuminate the tissue with at least three wavelengths, at least one of which must coincide with a water absorption peak, preferably at 980 nm. Thus, the radiation source 105 includes at least three radiation emitter modules of different wavelengths. The radiation source 105 and the detector 110 are placed directly in contact with the tissue to be examined. The radiation source 105 delivers the light to the tissue, and the detector 110 collects the optically attenuated signal back-scattered from the tissue.

The optical sensor 125 can produce radiation at wavelengths from about 650 nm to about 1000 nm. In one embodiment, the optical sensor 125 produces a range of radiation wavelengths. In this embodiment, the range of radiation wavelengths has at least a portion of the wavelengths between about 650 and about 1000 nm, such as between about 800 nm and about 950 nm. In another embodiment, the optical sensor 125 produces a range of radiation wavelengths including a wavelength of 880 nm. In another embodiment, the optical sensor 125 produces a range of radiation wavelengths including a wavelength of 660 nm. In this embodiment, the range of radiation wavelengths has at least a portion of the wavelengths between about 650 and about 1000 nm, such as between about 650 and about 800 nm.

Radiation between about 650 nm and about 1000 nm can be used to identify the position and quantity of hemoglobin in the tissue. Hemoglobin has a wide absorbance range, for both the HHb and $HbO_2$ states, in the range of about 650 nm to about 1000 nm. The isosbestic point between HHb and $HbO_2$ is about 808 nm. The isosbestic point is a specific wavelength at which two chemical species have the same molar absorptivity. Thus, HHb is believed to be the primary absorbing component in the range of between about 650 nm to about 808 nm and $HbO_2$ is believed to be the primary absorbing component in the range of between about 808 nm and about 1000 nm. At wavelengths below 650 nm, the absorption of hemoglobin is too high which would prevent anything but superficial measurement of the hemoglobin. At wavelengths above 1000 nm, the absorption of water is too high which would prevent measurement of absorption of either HHb or $HbO_2$. Using the absorbance ranges described above, the overall quantity of hemoglobin in an area can be determined while differentiating between HHb and $HbO_2$ in the same area.

A single measuring cycle of the optical sensor 125 includes the sequential switching on and off of the radiation source 105 that generates the light for a period of time T. During this period of time T, the tissue is stimulated by a radiation from the radiation source 105 characterized by a set of wavelengths $\lambda$ and by a constant intensity $I_i(\lambda)$; at the same time, the light exiting from the tissue, which has a mitigated intensity $I_o(\lambda)$, is measured by the detector 110. After time T, the radiation source 105 is switched off and the detector 110 integrates the detected signal for time T, with the aim of measuring the offset that had superimposed over the stimulation signal. Each radiation source 105 of the optical probe proceeds through the same cycle of switching on and off as described above. Once the switching on and off of all the radiation sources has been completed, the measuring cycle stops with a $T_{OFF}$ wait period during which the tissue is not stimulated and the data collected is processed. This data is then sent to the control unit that generates a graph or other information to be displayed on the device 150.

The device 100 may be connected to the secondary device 150 via a data transmission path 130. The device 100 includes a transmission and reception unit 120, and the secondary device 150 includes a transmission and reception unit 155. The transmission and reception unit 155 communicates via the data transmission path 130, which may be a wireless technology such as infra-red technology, Bluetooth or radio technology or the data transmission path 130 may be a wire. The data generated by the optical sensor 125 may be processed by a processor, such as a computer processor, in the device 100, and the processed data may be communicated to the secondary device 150 via the data transmission path 130. The processed data may be shown on a display 160 of the secondary device 150. The displayed processed data may be manipulated by the subject using control buttons 165, 170 on the secondary device 150. In another embodiment, the data generated by the optical sensor 125 may be sent to the secondary device 150 via the data transmission path 130, and then a processor, such as a computer processor, in the secondary device 150 may process the data. The processed data by the secondary device 150 may be shown on the display 160 and manipulated using control buttons 165, 170. Manipulations can include changing between data types or focusing on specific portions of the data. In a further embodiment, a portion of the data generated by the optical sensor 125 may be processed by the processor in the device 100 and the (partial) processed data may be communicated to the secondary device 150 via the data transmission path 130 for further processing by the processor in the secondary device 150. In a similar manner, the processed data may be shown on the display 160 and manipulated using control buttons 165, 170 in the secondary device 150. In another embodiment, the device 100 may operate as a single unit, wherein the data generated by the optical sensor 125 may be processed by the processor in the device 100, and the processed data may be communicated by a communication module (not shown) that sends a signal to the subject, such as an auditory signal, a visual signal, a vibratory signal, or combinations thereof, when a predetermined event occurs.

The device 100 can be used for the determination of muscle tissue movement based on the presence of and changes in concentrations of hemoglobin during exercise. The device 100 is configured to wirelessly measure real-time muscle parameters during both physical exercise and rest. The device 100 may be secured to a selected muscle group of the subject, such as the leg muscles of the vastus lateralis or gastrocnemius which are primary muscle groups of running and cycling. The optical sensor 125 in the device 100 uses a near infra-red light emitter and sensor pair to non-invasively quantify both the absolute concentration of oxygenated and deoxygenated hemoglobin as well as relative oxygenation saturation in the selected muscle group.

The device 100 can measure a variety of NIRS-derived measures related to the exercising muscle including the concentration of oxygenated hemoglobin [$HbO_2$]; the concentration of deoxygenated hemoglobin [HHb]; the total concentration of hemoglobin [tHb], which is the sum of [$HbO_2$] and [HHb]; and the Tissue Oxygenation Index (TOI), which is calculated using the following formulas:

$$TOI=[HbO_2]/[tHb] \text{ or } TOI\% = 100*([HbO_2]/[tHb]).$$

Muscles increase their oxygen requirements during periods of increased stress (e.g., athletic activity). The more a muscle is being stressed, the more oxygen is extracted from arterial blood to supply these needs. Therefore, an appreciable desaturation of hemoglobin occurs in stressed muscles, which correlates with exercise intensity. At the same time, at rest and under steady-state exercise conditions, there is a balance between blood lactate production and its subsequent removal. As the muscles are stressed to greater and greater degrees, more lactic acid is also produced as a byproduct. At a certain point (unique to each subject) the body begins producing more lactic acid than it can remove.

Further, the consecutive contraction and relaxation of skeletal muscles during exercise induces local changes of blood flow related to the alternating squeezing and release of the interspersed vasculature. This physical pressure acts in conjunction with a series of valves, which are present in the vasculature to prevent backflow of blood, to force the blood to continue along the path created by the vasculature and eventually back to the heart and lungs. Changes in blood flow due to muscular contractions generally follows the rhythm of the exercise, such as the rhythm of foot fall during jogging, as it correlates to the measured portion of the body. For example, when the gastrocnemius of the right leg is measured using the device 100, the changes in blood flow which locally correlate to the gastrocnemius of the right leg and, to a lesser extent, other muscles in the right leg will be visible to the device 100. Thus, the combination of the heart rate, the contraction/relaxation of local skeletal muscles, the intensity of the exercise and other physiological parameters are extractable from a time correlated measurement of NIRS-derived measures, such as [$HbO_2$], [HHb], [tHb] and TOI.

An exercise experiment was conducted with 40 subjects wearing the device 100 while exercising on a variable-speed treadmill. After warm-up, each subject was asked to choose a starting pace at which they could conduct a conversation with a running peer without fatigue. Then, the running pace was increased every 3 minutes by 20 seconds/mile (e.g., 8 min/mile, 7:40 min/mile, 7:20 min/mile, and so on). At the end of each running stage, the subject was asked to temporarily interrupt the run and to step aside of the treadmill to allow the examiner to take a capillary blood sample from the earlobe. The blood sample was chemically analyzed to provide the concentration of lactic acid or lactate (here indicated with [L]), accumulated in the bloodstream. After the subject reaches physical exhaustion, the subject was asked to walk on the treadmill for 5 minutes to recover.

During the running protocol in the exercise experiment, the device 100 measured the following NIRS-derived measures of the exercising muscle.
1. Concentration of oxygenated hemoglobin [HbO2];
2. Concentration of deoxygenated hemoglobin [HHb];
3. Total concentration of hemoglobin [tHb]

$$[tHb]=[HbO2]+[HHb]$$

Unlike the lactate analysis that is performed once at the end of each 3-min running stage, the NIRS-derived measures by the optical sensor 125 in the device 100 were continuously collected every 20 milliseconds. Filtering algorithms were applied to reduce short-term oscillations of the NIRS signals.

During running stages, muscular cells increased their oxygen consumption to create energy necessary to compensate muscle contraction, and subsequently frequent muscle contractions reduced blood flow supplied to the muscle through capillaries. As a result, [$HbO_2$] and [tHb] values decreased, while [HHb] increased. Furthermore, the rates at which these oxygenation variables change are distinct. Immediately after the start of the run, the oxygenation as measured by [$HbO_2$] and [tHb] drastically decreased for 20-30 seconds indicated by an increased rate of change of these variables. Subsequently, the muscle metabolism tended towards an equilibrium that induced more stable levels of oxygenation indicated by a relatively decreased rate of change of these variables. The time profile resembled an exponential decay.

Figure 2A:
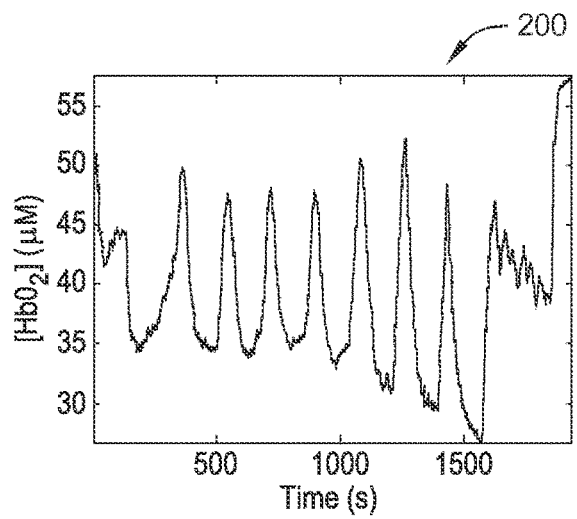
FIG. 2A illustrates a plot of the time course of the concentration of oxygenated hemoglobin, according to an embodiment described herein.
Figure 2B:
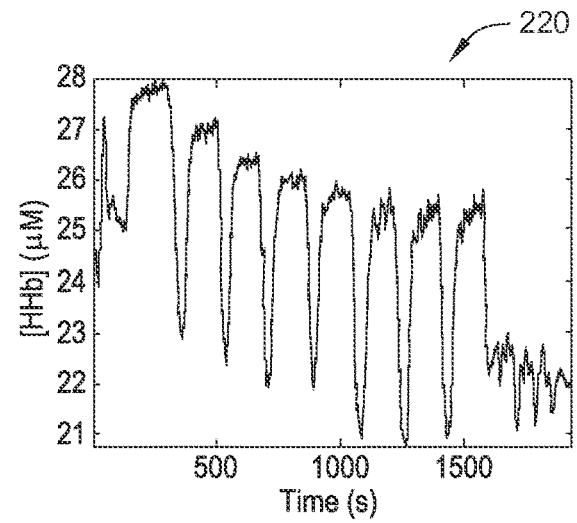
FIG. 2B illustrates a plot of the time course of the concentration of deoxygenated hemoglobin, according to an embodiment described herein.
Figure 2C:
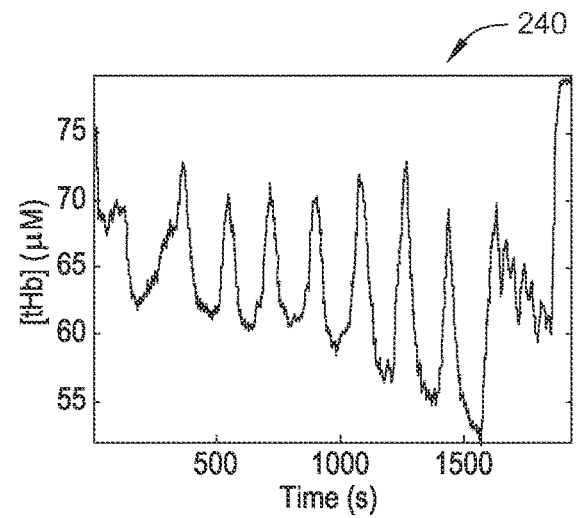
FIG. 2C illustrates a plot of the time course of the total concentration of hemoglobin, according to an embodiment described herein.

FIGS. 2A-2C illustrate a representative example of the NIRS-derived measures measured by the device 100 during the exercise experiment described above. FIG. 2A illustrates a plot 200 of the time course of the [$HbO_2$] of a subject jogging and stopping as described above. FIG. 2B illustrates a plot 220 of the time course of the [HHb] of a subject jogging and stopping as described above. FIG. 2C illustrates a plot 240 of the time course of the [tHb] of a subject jogging and stopping as described above. The time is measured in seconds (s) and the [HbO2] is measured in micromolar ($\mu M$).

During periods of temporary rest due to blood sampling, the muscle inactivity caused reduced oxygen consumption and the lack of contraction allowed the supply of oxygen-rich blood. Consequently, [$HbO_2$] and [tHb] increased rapidly, whereas [HHb] decreased. Furthermore, the rates at which these oxygenation variables change were distinct. Therefore, each running stage originated a specific signal change in each of the oxygenation variables associated with muscle desaturation, and each rest period favored the re-oxygenation of muscular tissues.

Measuring a NIRS-derived measure with a fast sampling frequency, such as a sampling frequency of less than or equal to about 100 ms, allows the subject to distinguish fluctuations related to a muscle contraction or other event. Many prior art devices and method employ a relatively low sampling frequency for NIRS-derived measures, such as sampling frequencies of 1 second or greater. The NIRS-derived measures from the prior art devices create an incomplete measure of the fluctuations, which may be an average of the various hemoglobin concentrations, and cannot be used to distinguish the fluctuations based on movement or exercise. By using a sampling frequency of less than or equal to about 100 ms, such as 20 ms, finer changes can be determined, such as changes in [$HbO_2$], [HHb] and [tHb] due to each muscle contraction during a jog, alongside changes over a longer period of time, such as changes in [$HbO_2$], [HHb] and [tHb] from the beginning to the end of a jog.

Figure 3:
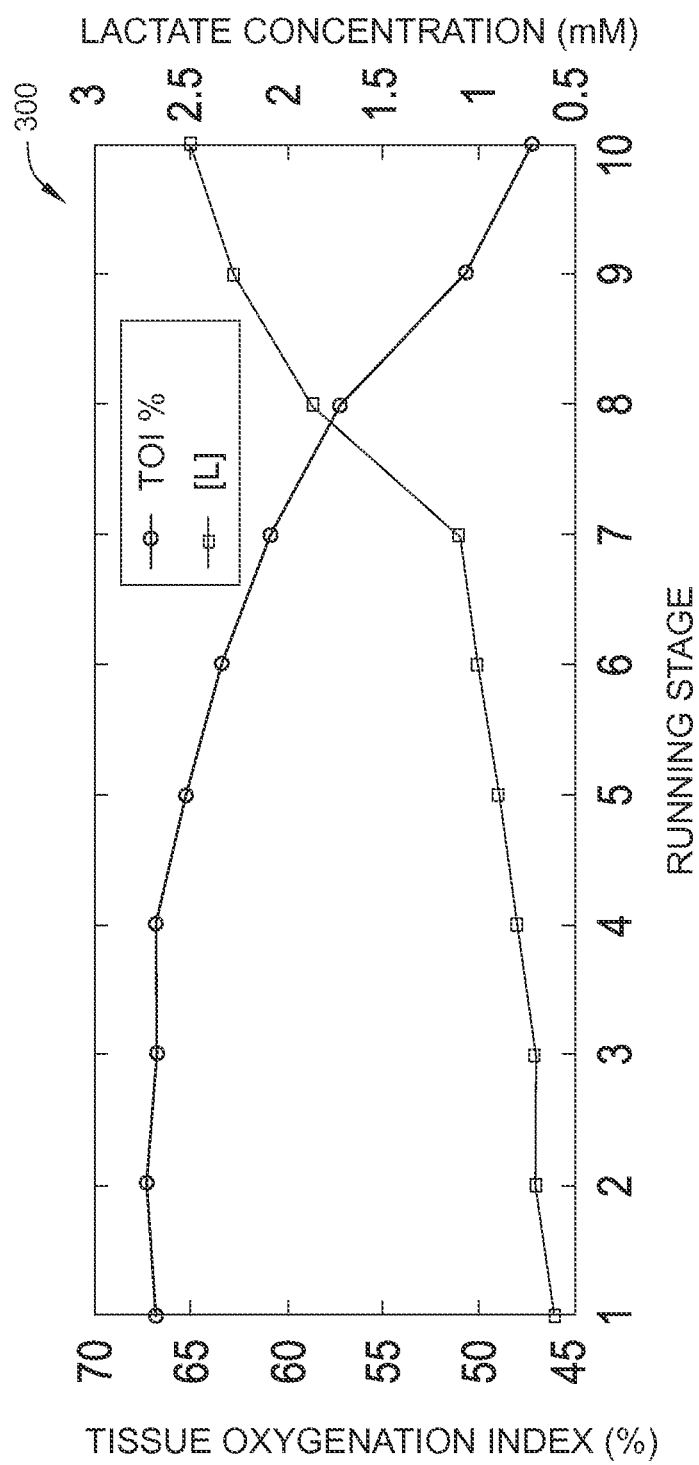
FIG. 3 is a graph of the correlation between the Tissue Oxygenation Index and the concentration of lactate, according to an embodiment described herein.

FIG. 3 illustrates a plot of the TOI alongside the concentration of lactate in a person, as a function of the running stage. The TOI is the percentile of the [$HbO_2$] available in the [tHb]. Changes in lactate concentration are believed to be an indicator of anaerobic exercise, or the ability of the cardiovascular system to meet the oxygen demands of the body. The lactate concentrations of the test subject were determined from the experimental samples of a subject, as described above.

Progressively, from stage 1 to stage 10, the increased oxygen demands of the measured muscle both decreased available oxygen in the blood stream, as detected by the NIRS device, and increased lactate concentration in the blood stream, as measured by the series of blood tests. Lactate concentration being a proxy for exercise intensity, the plot 300 shows a negative correlation between TOI and exercise intensity, as measured by lactate concentration.

Figure 4A:
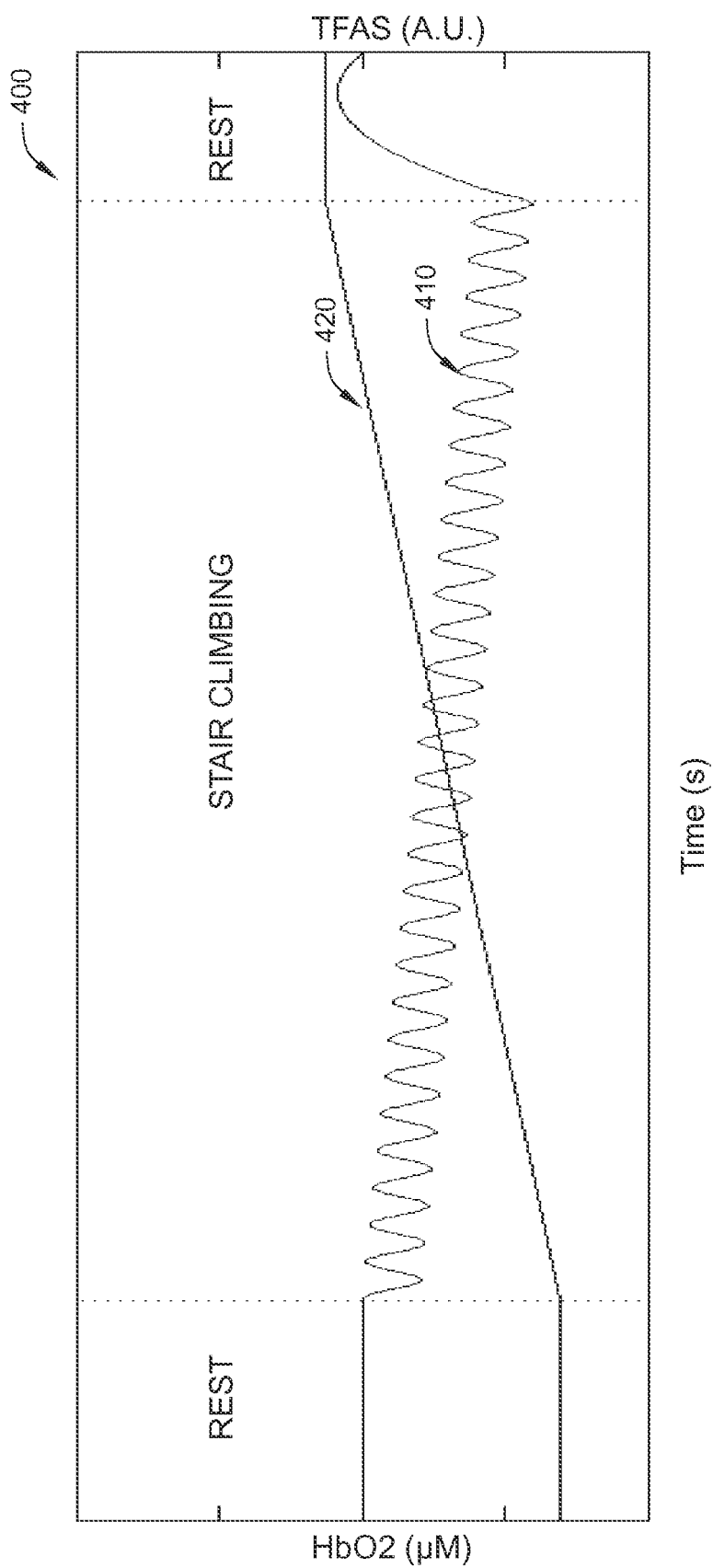

FIG. 4A is a plot 400 of $HbO_2$ as correlated to a strenuous physical activity, according to one embodiment. In this embodiment, the person climbed stairs over a period of time. [$HbO_2$] 410 was measured in micromolar ($\mu M$) using a NIRS device and the Time Frame Activity Score (TFAS) 420 which is shown in arbitrary units (A.U.), is calculated by adding all detected changes on the measured oxygenation variables collected during the measured time frame as compared to a baseline. The TFAS 420 can be over a specified standard time frame such as a day, a week a month or a non-standard time frame, such as 2 minutes shown with relation to FIGS. 4A and 4B. The plot 400 shows that stair climbing induced a consistent decrease in muscle oxygenation ([$HbO_2$] 410) due to the effort exerted by the legs during the workload. Simultaneously, each climbing step caused a biomechanical oscillation of [$HbO_2$] 410 synchronized to a muscle contraction detected by the NIRS sensor.

FIG. 4B is a plot 450 of $HbO_2$ as correlated to a moderate physical activity, according to one embodiment. In this embodiment, the person walked over a period of time. [$HbO_2$] 460 and TFAS 470 were measured as described in relation to FIG. 4A. The plot 400 shows that walking produced only a minimal decrease in muscle oxygenation ($HbO_2$ concentration) due to the effort exerted by the legs during the workload. Simultaneously, each step caused a change in local concentration of hemoglobin, as detected by the NIRS sensor, the change in local concentration synchronized to a muscle contraction. As shown by comparing FIGS. 4A and 4B, the measurement of one or more NIRS-derived measures during periods of exercise and rest can distinguish between intense exercise, moderate exercise and periods of rest.

Figure 5:
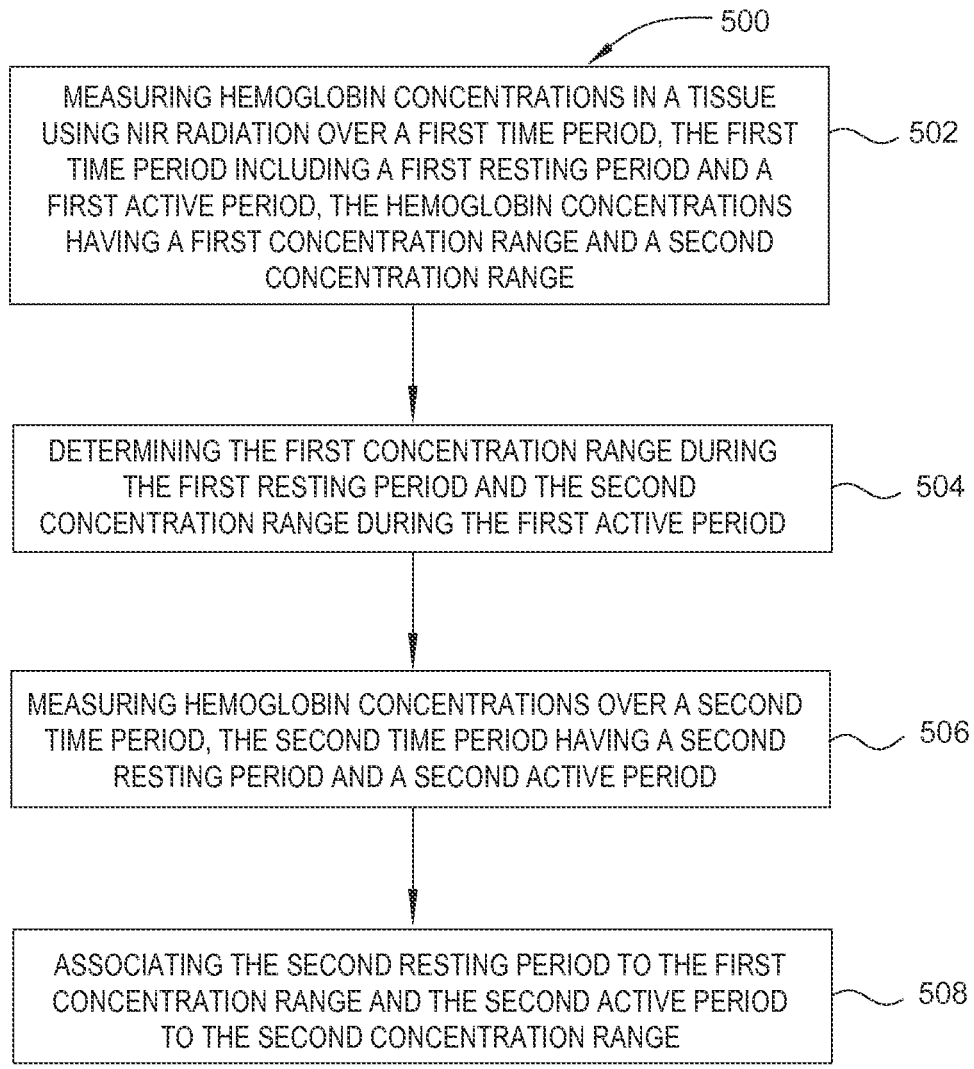
FIG. 5 depicts a block diagram of a method of measuring a biomechanical function, according to an embodiment described herein.

FIG. 5 is a flow chart of a method 500 of determining the presence of a biomechanical function, according to one embodiment. In some situations, the existence of activity is an important consideration to a clinician, such as after a trauma. By measuring changes in hemoglobin concentrations, such as [$HbO2$], [$HHb$] or [$tHb$], biomechanical function or activity can be determined grossly in the person.

The method 500 begins by measuring hemoglobin concentrations in a tissue using NIR radiation over a first time period at 502. The NIR radiation can be produced by a device, such as a NIRS device. As described above, the NIRS device emits radiation of a specific wavelength or range of wavelengths from a radiation source. The radiation passes through the tissue and is partially received by the detector. The absorbance of the radiation delivered over the first time period is indicative of various NIRS-derived measures, such as hemoglobin concentration. The first time period can be a relatively short time interval, such as 30 seconds, or a relatively long time interval, such as an interval measured in hours, days, weeks or months. The first time period includes at least one resting period and at least one active period. The resting period is a time period where at least the muscles local to the NIRS device are at rest. In one example, the resting period is a period of time prior to exercise where the person is lying supine. The active period is a time period where at least the muscles local to the NIRS device are engaged in an activity. In one example, the active period is a period of time during which the person is jogging. The hemoglobin concentration includes both a first concentration range and a second concentration range.

The first concentration range and the second concentration range are then determined using the first resting period and the first active period respectively, as in element 504. The hemoglobin concentration as measured by the NIRS device includes at least a partial oscillation based on rhythmic resting or active physiological event (e.g. the rhythm of a heartbeat, jogging, or jumping rope). Therefore, there will be a peak intensity and a trough intensity of the hemoglobin concentration which matches the speed and timing of the physiological event. Thus, the peak and trough intensities are indicators of the physiological event itself. Further, the peak intensity and trough intensity may vary over time or over the course of an activity. As such, a range of peak intensities and a range of trough intensities during rest can be applied to create a first concentration range while a range of peak intensities and a range of trough intensities during activity can be applied to create a second concentration range. The peak and trough intensities within the first concentration range can be correlated to one another and as a function of time to determine the related physiological event to the resting peak or trough intensity (e.g., a heartbeat or leg movement while otherwise at rest). The peak and trough intensities within the second concentration range can be correlated to one another and as a function of time to determine the related physiological event to the active peak or trough intensity (e.g., a leg movement while active).

The first concentration range and the second concentration range can be measured from a single resting period and a single active period, multiple resting periods and multiple active periods or combinations thereof. In one example, the first resting period is a single 10 minute resting period and the first active period is two 5 minute active periods. Further, the resting period and the active period may include a single type of rest and a single type of activity, multiple types of rest and multiple types of activity or combinations thereof. In another example, the first resting period is a resting period including a sitting rest and a supine rest and the first active period includes a jogging exercise. Combinations and permutations of the above can be used with embodiments described herein.

Once the first concentration range and the second concentration range are established, hemoglobin concentrations are measured over a second time period at 506. The second time period can correlate with daily activity of the person, such as from a NIRS device which is worn daily. The second time period can have a second resting period and a second active period. The hemoglobin concentrations as measured at the tissue will vary based on the activity or rest of the person, as well as by the intensity of the activity.

The second resting period is then associated to the first concentration range and the second active period to the second concentration range, as in element 508. The hemoglobin concentrations measured during the second time period are then evaluated using the first concentration range and the second concentration range to determine the time frame, duration and other parameters of the second active period and the second resting period. The second active period can correlate to multiple independent active times and the second resting period can correlate to multiple independent resting times. The second active period is a time period of activity for the subject and the second resting period is a time period of rest for the subject. The active times in the second active period and the resting times in the second resting time do not need to be contiguous. Further, though the first concentration range and the second concentration range are described as being determined only during the first period, this is not necessary. For example, the first concentration range and the second concentration range may be modified using data gathered during the second time period, such that changes in blood flow or oxygenation that are unrelated to activity or rest can be excluded.

In this embodiment, a previous determination of active and resting ranges are used to determine subsequent periods of activity. By performing a baseline measurement of the active periods and the resting periods using a NIRS device, ranges of hemoglobin concentration can be established. These ranges can then be applied to the person at a second time period to determine when the person is active or resting and for how long.

As described herein, at least two general types of analysis can be used to determine when the individual is active and what type of activity is being performed. The first analysis type is a frequency analysis. The frequency analysis is an analysis which compares the amplitude of specific frequencies to determine activity based on the occurrence of specific frequencies and to remove background frequencies. The frequency analysis can be performed on discrete portions of the transformed data. For example, a concentration over time graph can be separated into 10 second intervals or less which are then transformed to determine the frequency present. The frequencies determined from a first discrete portion can be applied to frequencies from a second discrete portion to determine activity and change in activity level. The frequency analysis can be applied to either a single device or multiple devices.

In one example of frequency analysis, a NIRS device detects a plurality of [tHb] at specific time intervals over a period of time creating a wave which is a function of concentration over time. This wave is transformed using a Fourier transform, thus creating a frequency based graph separating the frequencies which compose the wave and the amplitudes of each frequency. One or more frequencies can then be removed from the frequency based graph, such as frequencies which are known to correspond to resting background noise. The frequency based graph can then be converted back to a concentration over time wave to allow for better analysis of the concentration changes due to activity. In another example of frequency analysis, a concentration over time wave is created by detecting [tHb] at specific intervals over a period of time. This wave is transformed using a Fourier transform, thus creating a first frequency of a first amplitude, a second frequency of a second amplitude and a third frequency of a third amplitude. The first frequency can correspond to the change in the overall [tHb] over the entire period of time, such as would be seen in an exercising patient as they become more exhausted. The second frequency can correspond to a rhythmic activity and the pace of that activity, such as jogging at 3 steps a second. The third frequency can correspond to a change in that activity, such as jumping over a hurdle every 5 seconds during the otherwise rhythmic jog.

The second type of analysis is a time analysis. The time analysis is an analysis which compares a two or more measurement produced by different devices at the same time to determine when a specific physiological change has occurred, such as change from a resting state to an active state. In one example of time analysis, a NIRS device detects a first [tHb] at time 1, a second [tHb] at time 2, which is greater than the first [tHb], and a third [tHb] at time 3, which is less than the second [tHb]. These detected [tHb] can then be compared to one another or compared to previously determined ranges to detect when the person or a portion of that person is active.

In another example of time analysis in the context of a multiple device embodiment, a right leg NIRS device, a left leg NIRS device and a right arm NIRS device each detects a first [tHb], a second [tHb] and third [tHb] at three respective time points, creating a total of nine measurements. These detected [tHb] can then be compared between the devices to determine a rhythm of motion, such as the alternating rhythm of the right leg and left leg moving to run, based on the alternating timing as associated to the location of the detector. As can be seen when considering the time and frequency examples together, time and frequency can be used to determine function or activity, alone or in conjunction with one another. Further, time and frequency can be used on measurements derived from one or more devices.

Figure 6:
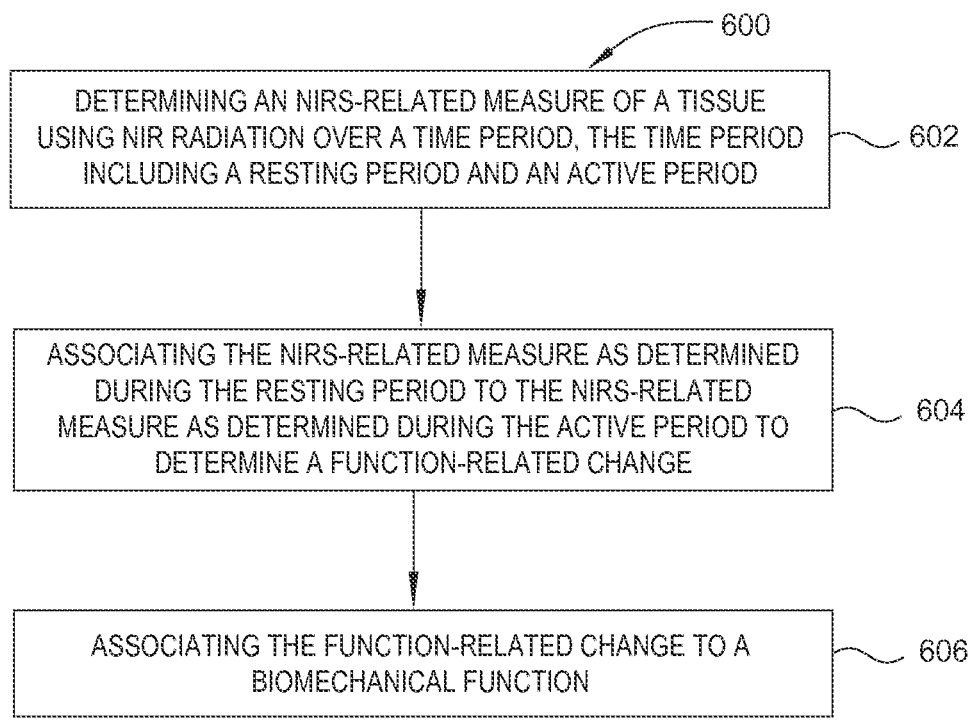
FIG. 6 depicts a block diagram of a method of determining the presence of biomechanical function, according to an embodiment described herein.

FIG. 6 is a flow chart of a method 600 of measuring a biomechanical function. Using the method described here, a specific biomechanical function can be determined based on NIRS-derived measures. A biomechanical function is generally defined as a movement or change in a portion of a person, such as an appendage, a muscle, a bone or other component. By measuring NIRS-derived measures using NIRS, a biomechanical function can be elucidated without having to observe the person. Further, the biomechanical function can be measured over time to provide time-correlated activity levels of a portion of the person.

The method 600 begins by determining a NIRS-derived measure of a tissue of a person using NIR radiation over a time period at 602. The NIR radiation can be produced by a device, such as a NIRS device. The NIRS-derived measure is a measurement related to available hemoglobin in a region of the body. The NIRS-derived measures can be oxygenation related data collected directly or indirectly by the NIRS device, such as blood flow, heart rate, [HbO$_2$], [HHb], [tHb] or TOI, as described with reference to FIGS. 1 and 2A-2C. Further, the NIRS-derived measure can be either processed data, as described above, or raw data, such as numbers correlating to the received signal at the detector. In one example, the first NIRS-derived measure is [tHb]. The NIRS-derived measure is then measured over a time period. The period of time can be a relatively short time interval, such as 30 seconds, or a relatively long time interval, such as an interval measured in months. The time period includes at least one resting period and at least one active period. The resting period is a time period where at least the muscles local to the NIRS device are at rest. The active period is a time period where at least the muscles local to the NIRS device are engaged in an activity. The detected NIRS-derived measure can be transmitted to a secondary device as described with reference to FIG. 1.

Next, the NIRS-derived measure as determined during the resting period is associated to the NIRS-derived measure as determined during the active period to determine an exercise-related oscillation, as in element 604. As described above, the muscles are more involved in blood mobility during activity. The muscles receive higher quantities of blood from the heart during activity. The blood is squeezed from the muscles during periods of muscle contraction. When the muscle relaxes, the blood flows back into the muscles based on both cardiac activity and blood pressure. As such, [HbO$_2$], [HHb], [tHb] and TOI are oscillation-like with relation to the activity. Thus, the changes over time in [HbO$_2$], [HHb], [tHb] and TOI have both a rhythm and an intensity which relates to the speed of the activity, the type of activity and the intensity of the muscle contractions. During the resting period, autonomic activities such as heart beat will control the ebb and flow of blood. As autonomic activities are constantly occurring during both the resting period and active period, the measurement of the NIRS-derived measure over the resting period will help distinguish when exercise-related NIRS-derived measure changes occur. Autonomic activities and other related events are the background oscillation. The change in NIRS-derived measures over the active period excluding background oscillation is the function-related change. The function-related change may be an oscillation or have oscillation-like characteristics.

The function-related change is then associated to a biomechanical function, as in element 606. A biomechanical function is an interaction of the person with the environment in relation to the contraction or extension of a muscle, such as the movement of a leg during exercise. The function-related change is a cardiovascular indicator of a specific contraction, extension, movement or combinations thereof. The function-related change can be directly related to the local movement (e.g., contraction of a muscle in an arm or leg) for the exercise or activity. Therefore, the function-related change is a direct indicator of activity in a portion of the subject.

The function-related change can incorporate secondary data to provide more in depth information on the activity of the subject in some embodiments. Secondary data is data derived from a secondary device which may be related to activity or rest, such as data from an accelerometer or a GPS device. The secondary data can then be used to calculate speed, stride length, acceleration, force applied on each stride or other information based on information derived from the NIRS device. The exercise-related change can then be applied to a specific activity, such as jogging, running, jumping rope or others. In another embodiment, the function-related change at a tissue measured by a single NIRS device can be applied to determine the specific activity of a remote subject.

In one example, a NIRS device is positioned over the gastrocnemius of a person with the optical probe positioned to detect [tHb] in the gastrocnemius. The NIRS device collects data on the [tHb] in a continuous or semi-continuous fashion over a time period of an hour. During the hour time period, the person jogs at a rate of 5 mph for 5 minutes. The information collected by the NIRS device during the jogging and the rest are then applied to [tHb] detected at a later time period to determine whether the leg of the person, and by extrapolation the person, is resting or performing a specific activity. The information can be applied directly, such as by associating the rhythm of the [tHb] change and the intensity of the [tHb] from the jog/rest cycle to the later time in a constantly updated fashion, or indirectly, such as by determining a general rhythm for the subject from the rhythm of the [tHb] change and the intensity of the [tHb] during the jog/rest cycle which can be applied to the later time period. The determination of activity in the leg can be inferred or calculated from the intensity of the [tHb] detected as compared to baseline, the change in [tHb] from a previous measurement, [HbO$_2$] or [HHb] as related to the [tHb], or other factors derived from the prolonged measurement.

The NIRS-derived measures are believed to have a rhythm that can be attributed to activity generally by that muscle. The muscle is believed to have a specific formation, contraction speed, contraction strength, vascularization and other factors which determine the hemoglobin concentrations available to the region as well as standard changes which can occur due to contraction. Once determined, this rhythm can be used to determine when the muscle in question is exercising and when it is resting.

The embodiments herein are described in relation to converted optical measurements (e.g., [tHb]), rather than raw data (e.g., the absorption detected at a detector of a specific wavelength of light). However, raw data may be used in place of or in combination with converted optical measurements to determine the existence or intensity of a biomechanical function or biomechanical activity. Further, though the tissues focused on are generally muscular tissues, other tissues may be used to make the same determinations of function-related change. For example, vasculature which is embedded in a tissue which is proximate a muscle group is expected to have an increase in blood flow and pressure during the contraction of the muscle. The detected NIRS-derived measures in the nearby vasculature can be used to determine function-related changes in the nearby muscle or muscle groups.

Long term activity data can be useful for rehabilitation or for increasing athletic performance. By gathering data related to a NIRS-derived measure according to the methods above, the movement of a specific portion of the body may be determined without being able to view the subject. Therefore, information related to exercise can be gathered empirically without interfering with a subject's daily life.

Figure 7:
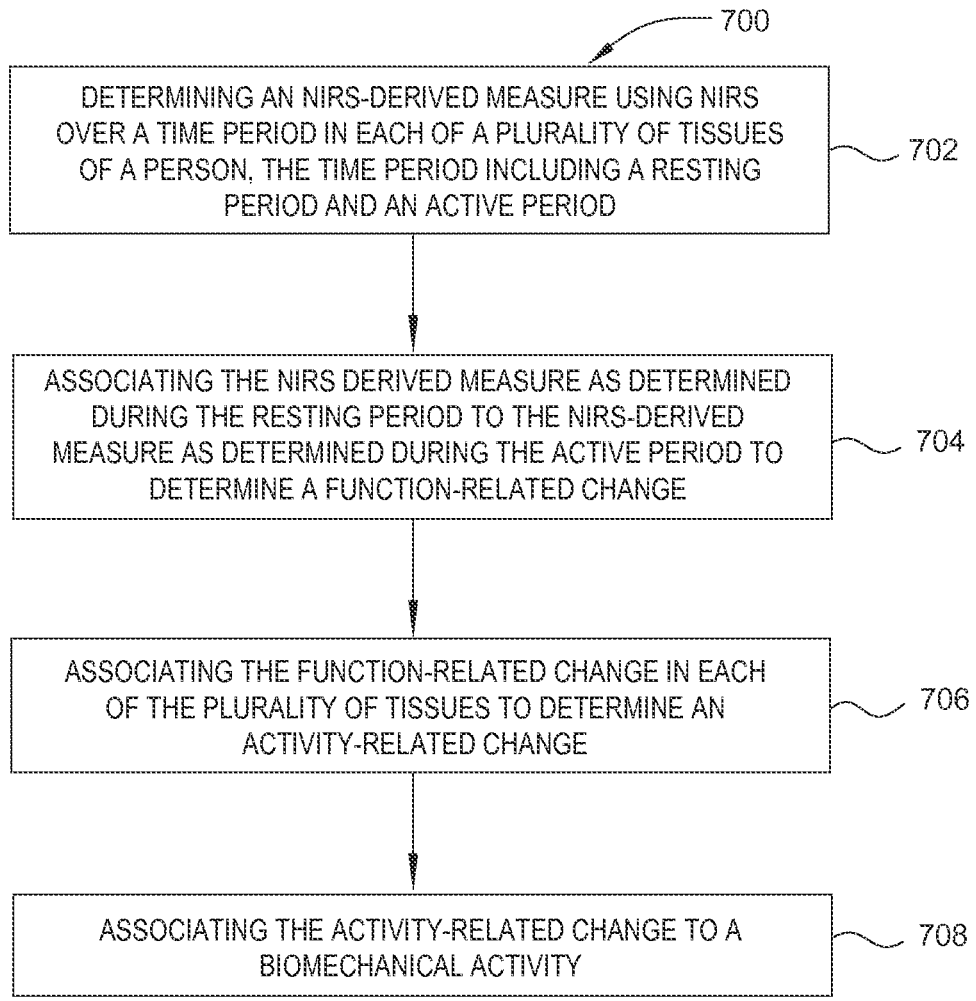
FIG. 7 depicts a block diagram of a method of measuring biomechanical activity, according to an embodiment described herein.

FIG. 7 depicts a block diagram of a method 700 of measuring biomechanical activity, according to one embodiment. In some instances, it may be beneficial to determine both the biomechanical function and the biomechanical activity of the person. Biomechanical activity, as differentiated from biomechanical function, is the interaction of one or more biomechanical functions for one unified event. In one example, the flexing of the rectus femoris may indicate the movement of a leg as a biomechanical function which acts in conjunction with numerous other biomechanical functions involved in the biomechanical activity of running. By detecting NIRS-derived measures, and thus biomechanical function, at multiple sites, a biomechanical activity can be determined.

The method 700 begins with determining a NIRS-derived measure using NIRS over a time period in each of a plurality of tissues of a person at 702. Here, multiple NIRS devices can be positioned at different locations on the body. The NIRS devices can be positioned on random muscles or muscle groups. In another embodiment, the NIRS devices are positioned strategically to detect a specific type of biomechanical function/activity or to provide a broad range of detection. The time period can include a resting period and an active period, as described with reference to FIG. 6. In one example, a plurality of NIRS devices is positioned to receive oxygenation information from each bicep and each gastrocnemius of a person.

The NIRS-derived measures as determined during the resting period can then be associated to the NIRS-derived measure as determined during the active period to determine a function-related change at 704. The function-related change can be determined as described above with relation to FIG. 6. The function-related change is determined in each tissue with a connected NIRS device. The NIRS-derived measures in each tissue are expected to vary based on the contraction and extension of the tissues being monitored. Thus, the function-related change at one tissue may have different timing or rhythm than the function related change at another tissue.

In the example above, the NIRS device positioned on each gastrocnemius and on each bicep collects oxygenation information such as during a resting period and during a run. During the resting period, the oxygenation information is expected to be largely the same. During the active period, the oxygenation information is expected to vary based on which muscle is contracting or extending. Here, each muscle is expected to have a function-related change which may have different timing, intensity or combinations thereof than another.

The function-related change in each of the plurality of tissues is then associated to one another to determine an activity-related change at 706. The function-related changes are then combined to create an activity-related change. The function-related change in the NIRS-derived measure over a time period can be associated to other function-related changes over the same time period to create an activity related change. This activity-related change includes the timing of the changes in blood pressure and blood flow rate between different measured tissues, increases or decreases in oxygenation between different measured tissues and other factors.

The activity-related change is then associated to a biomechanical activity at 708. As described above, the function related changes are attributable to a specific biomechanical function. The biomechanical functions as a whole provide an indication as to what biomechanical activity is being performed, as well as the rate of activity, the intensity of activity and other factors which can be extrapolated from the function-related change. In one embodiment, an increase in [tHb] in the right bicep followed by an increase in [tHb] in the left gastrocnemius may indicate that a person is jogging.

In this embodiment, the function-related change at a first device is described as being combined with other function-related changes as measured using at least a second device to determine the activity-related change. The activity-related change is then used to determine the biomechanical activity. However, function-related change may provide information about the biomechanical activity such that the use of a second device or determination of the activity-related change is unnecessary. In one embodiment, the oxygenation information is collected from the tissue such that the function-related change provides two distinguishable sets of information, which is indicative of the activity involved. In one example, changes in a NIRS-derived measure when a person hits the ground alongside the contraction of the muscle in a first activity, such as jumping rope, can be used to determine the difference between the first activity and a second activity, such as jogging. It is expected that a person would land with more weight during jogging than during jumping rope, as the jogger is landing with a single foot where the person jumping rope is landing with both feet. As such, the landing between the two exercises can create a secondary wave which is distinguishable. In another embodiment, the function-related change is distinct from other types of function-related change and based on the location measured only one activity or type of activity is possible (e.g., a specific blood flow pattern taken from a bicep known to be characteristic of a "push-up").

Some individuals may benefit by a more complete analysis of daily activity including type of activity. By following a group of biomechanical functions based on NIRS-derived measures as measured using a plurality of NIRS devices, the type and intensity of a biomechanical activity can be determined. This information can be used to speed rehabilitation, help athletes perform better or assure compliance with a workout routine.

Figure 8:
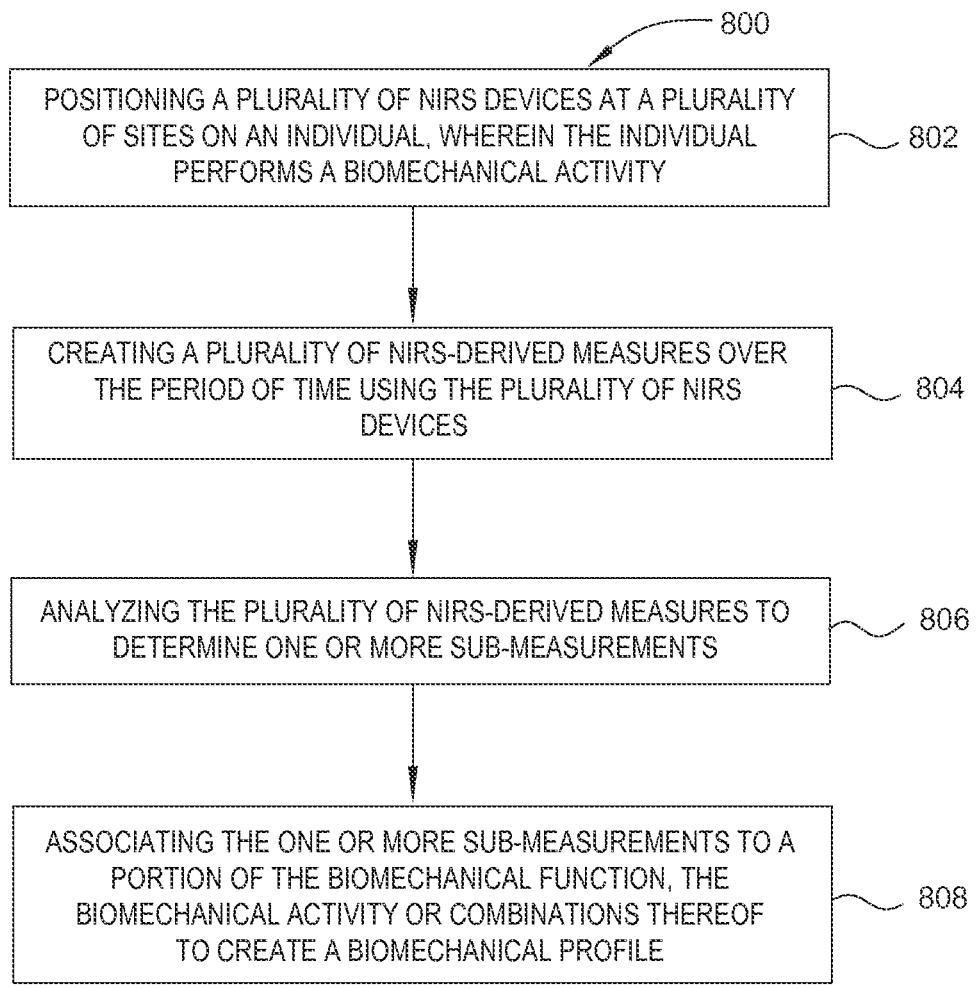
FIG. 8 depicts a block diagram of a method of creating a biomechanical profile, according to an embodiment described herein.

FIG. 8 depicts a method 800 of forming a biomechanical profile from measured biomechanical activity, according to one embodiment. A biomechanical profile is correlated information about the individual to determine changes from a baseline state. The biomechanical profile is created using information from the rhymicity and intensity of biomechanical functions as associated to biomechanical activities, such that an unrelated biomechanical activity can be determined from a biomechanical function. The biomechanical profile can be used to detect a disease state, differentiate between forms of the same biomechanical activity, and determine unknown biomechanical activities. The method 800 can include positioning a plurality of NIRS devices at a plurality of sites on an individual, wherein the individual performs a biomechanical function or a biomechanical activity, the biomechanical activity correlating with rhythmicity measures and intensity measures from one or more muscle groups, at 802; creating a plurality of NIRS-derived measures over a period of time using the plurality of NIRS devices, at 804; analyzing the plurality of NIRS-derived measures to determine one or more measurement features, at 806; and associating the one or more measurement features to a portion of the biomechanical function, the biomechanical activity or combinations thereof to create a biomechanical profile, at 808.

The method 800 begins by positioning a plurality of NIRS devices at a plurality of sites on an individual, wherein the individual performs a biomechanical function or a biomechanical activity, at 802. The biomechanical function or the biomechanical activity can be determined as described with reference to FIG. 6 or 7 respectively. The biomechanical function and the biomechanical activity, being a combination of biomechanical functions, include one or more rhythmicity measures and intensity measures for one or more muscle groups. A rhythmicity measure is a measure of NIRS-derived measure change as it relates to the rhythmical quality or character of the NIRS-derived measure over time. An intensity measure is a measure of the force applied in a biomechanical function.

Next, a plurality of NIRS-derived measures is created over a period of time using the plurality of NIRS devices, at 804. Here, a plurality of NIRS devices can be positioned at different locations on the body. The NIRS devices can be positioned on or near random muscles or muscle groups. In another embodiment, the NIRS devices are positioned strategically to detect a specific type of biomechanical function/activity or to provide a broad range of detection. The plurality of NIRS devices provide a plurality of NIRS-derived measures as associated to the NIRS device location. The plurality of NIRS-derived measures may each be a continuous measurement over time, a pulsatile measurement over time or in another fashion such that components of the NIRS-derived measures can be internally differentiated. As above, the plurality of NIRS-derived measures may also include changes in wavelength or spectrum of wavelengths used in detection. The plurality of NIRS-derived measures can be taken during a biomechanical function, a biomechanical activity, a resting period or combinations thereof. In one embodiment, the plurality of NIRS-derived measures is taken over a period of time including two biomechanical activities and a rest period.

The plurality of NIRS-derived measures is then analyzed to determine one or more measurement features, at 806. Measurement features are component measurements related to both physiology of the individual, the type and intensity of an exercise, disease state (if any), or other factors that come together to create a NIRS-derived measure at a point in time and the plurality of measurements over the period of time. Measurement features can include rhythmicity measures and intensity measures. Rhythmicity measures are determined based on rhythmic fluctuation in the NIRS-derived measure at the detected site as determined from the NIRS-derived measure. The intensity measure is measured by using increase in hemoglobin volume in a region, speed of increase in volume or flow and other pressure related indicia derived from the NIRS-derived measure as a proxy for intensity of the contraction. Measurement features as described here can be extrapolated from the NIRS-related measure using time domain or frequency domain analysis as described with reference to FIG. 5.

In one embodiment, four NIRS devices are positioned on an individual, two on each leg at bilateral positions. The individual performs two biomechanical activities, such as jogging and jumping rope. The plurality of NIRS-derived measures is collected during the biomechanical activities and during any intervening rest cycles over a period of time.

The plurality of NIRS-derived measures is then analyzed to separate one or more measurement features. In this example, the rhythm of the jumping detected at NIRS device 1 is expected to differ from the rhythm of the jogging detected at the same device. The rhythm difference may be attributable to feet hitting the ground, muscle contraction proximate to the NIRS device, muscle contraction distal to the NIRS device, increases in heart rate or other factors. Further differences in rhythm are expected to be detected at NIRS device 2, 3 and 4. The different rhythms can then be separated to determine their individual contribution to the overall measurement at a specific period of time. In further embodiments, the different rhythms can also be used to determine the location of the contributing factor (e.g., which distal muscle is likely the source of the change in rhythm).

Alongside the difference between the rhythms, the difference in intensity can be determined. In this example, the intensity of the jumping detected at NIRS device 1 is expected to differ from the intensity of the jogging detected at the same device. The intensity difference, as with the rhythm difference, may be attributable to feet hitting the ground, muscle contraction proximate to the NIRS device, muscle contraction distal to the NIRS device, increases in heart rate or other factors. Further differences in intensity are expected to be detected at NIRS device 2, 3 and 4. The different intensity can then be separated to component intensities to determine their individual contribution to the overall measurement at a specific period of time. In further embodiments, the different intensities can also be used to determine the location of the contributing factor (e.g., which distal muscle is likely the source of the change in rhythm).

The one or more measurement features are then associated to a portion of the biomechanical function, the biomechanical activity or combinations thereof to create a biomechanical profile, at 808. As described above, the measurement features relate directly or indirectly to a biomechanical function, a biomechanical activity or combinations thereof. Each of the sub-measures can be associated to a specific portion of the biomechanical function or activity. In one example, a second weaker rhythm which oscillates slightly later temporally than a first stronger rhythm may be associated with a movement of a muscle upstream of an artery which travels through the detection site. The second weaker rhythm can then be separated from the first stronger rhythm to create a sub-measurement. Portions of this sub-measurement, such as peaks and troughs, effects on oxygenation at the downstream site and other components of the sub-measurement can them be associated to an unrelated or unknown biomechanical activity or function to determine what the activity is. This sub-measurement can then be used with other measurement features, which can be determined from the original NIRS-derived measure or other NIRS-derived measures, to determine both type and intensity of the activity based known NIRS device position.

The measurement features and the associated portion of the biomechanical function or activity can be combined to create a biomechanical profile for the individual. Thus, the measurement features of the biomechanical function provide generically extrapolatable data which can be attributed to a portion of an unknown or unrelated activity. The biomechanical profile can further be used to measure intensity changes over time (e.g., the individual's right leg performed better a week ago that present performance), differences between portions of the body (e.g., the individual's right leg output is not matching the individual's left leg output), changes in endurance, or other performance related issues.

CONCLUSION

Methods described herein disclose the use NIRS to provide a time correlated view of NIRS-derived measures in one or more tissues. By collecting data on NIRS-derived measures using NIRS radiation, activity generally, as well as specific activities and functions, can be differentiated over the time period without viewing the person and in a non-invasive fashion. By knowing when activities are performed, compliance with an exercise routine can be established empirically and corrections can be made accordingly. Further, by determining specific activities and functions being performed, training regimens can be adjusted to assure that a person physically develops according to their goals.

While the foregoing is directed to embodiments of the present invention, other and further embodiments of the invention may be devised without departing from the basic scope thereof, and the scope thereof is determined by the claims that follow.

The invention claimed is:

1. A method of measuring physiological parameters, comprising:
 measuring hemoglobin concentrations in a tissue using near infra-red (NIR) radiation over a first time period, the first time period including a first resting period and a first active period, the hemoglobin concentrations having a first concentration range and a second concentration range;
 determining the first concentration range during the first resting period and the second concentration range during the first active period;
 measuring hemoglobin concentrations over a second time period, the second time period having a second resting period and a second active period;
 associating the second resting period to the first concentration range and the second active period to the second concentration range, wherein the second active period and second resting period are incorporated into a time frame activity score; and
 displaying the time frame activity score to a user.

2. The method of claim 1, wherein the hemoglobin concentrations are a function of the ratio of the concentration of deoxygenated hemoglobin [Mb] over the concentration of oxygenated hemoglobin [HbO2].

3. The method of claim 1, wherein the hemoglobin concentrations are measured in a plurality of tissues.

4. The method of claim 1, wherein high concentration range and the low concentration range incorporate measurements from an accelerometer or a GPS device in associating the second resting period to the high concentration range and associating the second active period to the low concentration range.

* * * * *